United States Patent
Brother et al.

(10) Patent No.: US 6,485,446 B1
(45) Date of Patent: Nov. 26, 2002

(54) PROTECTIVE APPAREL COMPRISING AN ENERGY IMPACT ABSORBING POLYMERIC MATERIAL AND METHOD FOR SHAPING SAID MATERIAL

(75) Inventors: Theodore B. Brother, Andover; Roy M. Cowdrey, Greenfield; Michael D. Nichols, Gardner, all of MA (US)

(73) Assignee: I-Tek, Inc., Lawrence, MA (US)

( * ) Notice: Subject to any disclaimer, the term of this patent is extended or adjusted under 35 U.S.C. 154(b) by 0 days.

(21) Appl. No.: 09/583,355

(22) Filed: May 31, 2000

Related U.S. Application Data

(63) Continuation-in-part of application No. 09/461,987, filed on Dec. 15, 1999.

(51) Int. Cl.[7] .................................................. A61F 5/00
(52) U.S. Cl. .............................. 602/20; 602/5; 2/455; 2/456; 2/462; 2/463
(58) Field of Search ........................ 602/13, 23, 30, 602/65; 128/882; 601/152; 2/239, 22, 240, 267, 455–456, 462–463

(56) References Cited

U.S. PATENT DOCUMENTS

| | | | | |
|---|---|---|---|---|
| 4,252,910 A | * | 2/1981 | Schaefer | 521/145 |
| 5,432,000 A | * | 7/1995 | Young, Sr. et al. | 428/372 |
| 5,501,659 A | * | 3/1996 | Morris et al. | 602/27 |
| 5,596,770 A | * | 1/1997 | Kunesh | 2/239 |
| 5,625,896 A | * | 5/1997 | LaBarbera et al. | 2/22 |
| 5,869,164 A | | 2/1999 | Nickerson et al. | 428/76 |

* cited by examiner

Primary Examiner—Michael A. Brown
Assistant Examiner—Lalita M. Hamilton
(74) Attorney, Agent, or Firm—Nields & Lemack

(57) ABSTRACT

Protective body apparel, comprising, one or more foundation components adapted to be removably worn proximate one or more parts of said body; and one or more pads comprising, a polymeric material capable of absorbing impact energy, which comprises a plurality of microspheres and which is viscoelastic at room temperature, wherein one or more of said pads is carried by one or more of said foundation components; and method for shaping said polymeric material.

13 Claims, 3 Drawing Sheets

PROTECTIVE APPAREL COMPRISING AN ENERGY IMPACT ABSORBING POLYMERIC MATERIAL AND METHOD FOR SHAPING SAID MATERIAL

CROSS-REFERENCE

This is a continuation-in-part of U.S. patent application Ser. No. 09/461,987, filed on Dec. 15, 1999.

FIELD OF THE INVENTION

This invention relates to protective apparel comprising an energy impact absorbing polymeric material and method for shaping the material.

BACKGROUND OF THE INVENTION

Manufacturers and designers of protective gear and apparel are always striving to develop a product which provides the maximum amount of protection for the least amount of cost while optimizing fit and flexibility of movement. With regard to impact protective gear and apparel, such as bullet-proof (ballistic) vests or elbow or shin guards, the rigid surface material on the outer surface of such gear or apparel does not absorb the major force of the impact. The energy of impact is transferred through the rigid material and is passed through to the underlying material and subsequently to the body, causing bruising or impact trauma. In the case of body armor, such as bullet-proof (ballistic) vests, multiple layers of Kevlar® and Spectra® woven fabric are typically encased within a fabric shell and are collectively referred to as a "ballistic pack". As a bullet leaves the barrel of a rifle or pistol, it not only has a high rate of forward velocity, it also spinning at a high rate of speed due to the rifling of the barrel. As the bullet enters the Kevlar, it becomes entangled in the Kevlar fibers and its forward motion is stopped. Allow this action prevents the bullet from penetrating the body, it does not dampen or absorb the transfer energy of the impact. It is this transferred energy that causes bruising and impact trauma in and around the area of impact.

In an effort to reduce impact trauma, trauma packs are used in conjunction with the ballistic packs. These trauma packs are typically constructed from the same Kevlar® or Spectra® fabric used in the ballistic packs but are made up of layers which are thinner than the layers in the ballistic packs. The thinner layers in the trauma pack are either laminated together or saturated to hold them together. However, these trauma packs add substantial weight, decrease the flexibility of the vest and, thus, the movement of the wearer.

With regard to other types supporting and cushioning apparel and protective gear, at present, foam pads are generally the primary means utilized by manufacturers to reduce injury. However, foam merely flattens directly under the point of pressure and does not redirect the pressure or energy of the impact. Although foam acts as a shock absorber, it is incapable of acting as an energy absorber. Foam does not flow or conform to specific shapes. Foam merely compresses and flattens under an external load. Using foam as a cushioning material and to merely cover tender spots results in restricted circulation and does not reduce discomfort and bruising.

Shock absorbing materials such as foam compress so quickly under pressure that they are unable to absorb enough energy to significantly reduce impact trauma. Thixotropic liquids such as those described in U.S. Pat. No. 5,869,164 to Nickerson, which is a mixture of microspheres in oil and a thickener, are heavy in weight and, because they comprise a liquid medium, they are non-compressible and therefore behave like a supporting device and do not reduce trauma or provide impact protection. As such, although shock absorbers reduce the risk of surface injury, they do not significantly reduce injury to the underlying tissues because a substantial portion of the energy is transferred to the underlying tissues. Furthermore, such liquid based devices are subject to puncture and leaking and are difficult to manufacture because of their complex formulations.

In addition, although it is described in U.S. Pat. No. 5,869,164 that glass and plastic microspheres may be mixed with thixotropic liquids, the microspheres are merely suspended in the thixotropic liquid and thus are free to move around within the liquid. This freedom of movement allows the microspheres to be pushed to, and concentrated in, areas of the thixotropic liquids which are not subjected to pressure. Movement of the microspheres thus reduces the effectiveness, especially over extended periods of use, of thixotropic liquids.

Moreover, bonding agents, such as polyisobutylene polymers, which are typically used in such cushioning devices, are almost always non-liquid at room temperature because of the molecular weight, chemical composition and thermoplasticity. As such, before working with these polymers and to make them flowable, the temperature of these polymers must be raised to lower their viscosity.

Resilient, conforming materials comprising microspheres are also described in U.S. Pat. No. 4,252,910 to Schaefer. Specifically, Schaefer describes a material in which gas-filled microspheres are cohered to a mass by a bonding agent; wherein Schaefer's microspheres consist of an elastic copolymer preferably of vinylidene chloride and/or vinyl chloride copolymerized with acrylonitrile. However, the formulations of Schaefer have such a high viscosity, a high moisture content and sticky nature make the resulting materials virtually impossible to handle and are useless for most applications. For example, Schaefer's material is non-liquid at room temperature and, according to Schaefer, the user must warm his or her foot above normal body temperature to soften Schaefer's material enough to take the shape of the user's foot. Moreover, Schaefer teaches that his material must be at least at body temperature to be flowable. In addition, Schaefer's material has a very high ratio of polymeric material to microspheres, namely, about 53:1. Furthermore, Schaefer is unable to substantially increase the number of microspheres per unit volume because of the high viscosity of Schaefer's material. The low number of microspheres in Schaefer's material severely limits the number of interstices per unit volume which, in turn, reduces the dilatency of Schaefer's material.

A further disadvantage of polyamide and polyisobutylene synthetic polymers as a binding agent is that the resulting cohered mass of microspheres shows a high degree of compression set (low compression regain) which limits the mass' usefulness. This is especially true when such materials are used in cushioning applications.

Furthermore, to date there are no previously known methods for processing materials such as Schaefer's mass into predetermined shapes. Contrary to Schaefer's disclosure, in practice, it is impractical to fill an envelope with Schaefer's material, especially any type of film through which moisture vapor can be transmitted. Schaefer's material has such a high moisture content that, if encapsulated in a film through which moisture can be transmitted, Schaefer's material will lose moisture over time which will change the physical characteristics of Schaefer's material. Schaefer's material also cannot be rolled, pressed or extruded because Schaefer's mass is too viscous, too sticky and has a very high resistance to pressure due to its dilatent characteristics. Schaefer's mass will act as a cushion and will only conform to an externally applied pressure as long as the applied pressure is applied a slow, constant, low force rate.

Moreover, whenever welding or sealing plastic envelopes, it is important to ensure that the plastic film to be sealed is clean and free of contaminants, especially in the area to be sealed. When encasing flowable materials, such as Schaefer's material, there is the added problem of containing the flowable material while the film is being sealed. Previously, the only possible way to encapsulate such materials was to drop the material into a pre-made envelope which is sealed on three sides and then sealing the entry side after the material is introduced. However, this method is impractical and does not sufficiently overcome all the problems, for example, the flowable, moist materials are heavy because they comprise water and/or oil, they leak, they often contain solvents which are flammable, they separate into solid and liquid phases, they are adversely affected by temperature (water freezed, oil thickens), they cannot be incorporated into a dual density construction with other padding materials such as foam, and they are capable of supporting bacterial growth because of their high moisture content.

SUMMARY OF THE INVENTION

It is therefore a primary object of this invention to provide protective gear and protective apparel comprising an impact energy absorbing, viscoelastic, polymeric material having low density and a shape adapted for use with the gear and apparel.

It is a further object of this invention to provide a cost-effective method for processing viscoelastic, polymeric material at room temperature into a predetermined shape.

It is further object of this invention to provide a method for preparing a continuous sheet of polymeric material, which is viscoelastic at room temperature, at any length, having a uniform thickness and width.

It is a further object of this invention to provide a in-line method for processing viscoelastic, polymeric material at room temperature into a predetermined shape.

It is a further object of this invention to provide protective apparel comprising an impact energy absorbing material which, at room temperature, conforms to the user's body and compresses under pressure and yet is capable of substantial regain when the pressure is removed.

It is a further object of this invention to provide a vest-like device, such as a ballistic or bullet-proof vest, which can be worn about the torso, having one or more pockets integral with or at least partially fixed to the device which contain a viscoelastic, polymeric material capable of absorbing the impact energy of a bullet or other such ballistic material.

It is a further object of this invention to provide a vest-like device to which one or more pockets or overlays are attached in a manner which does not restrict the elasticity or flexibility of the device; wherein the pockets or overlays contain pads or cells comprising an impact energy absorbing, viscoelastic, polymeric material; and wherein the pads or cells may further comprise one or more of the following, bonded elastic microspheres, foam, gel, liquid, gas or other suitable cushioning materials.

It is a further object of this invention to provide a trauma pack, for use in conjunction with a ballistic pack, that is thinner, lighter, more flexible and less expensive than currently used trauma packs made from layers of aramid fibers and used in conjunction with ballistic packs.

The compressive material of the invention provides numerous advantages over currently available supporting, cushioning and protective materials adapted for use in protective gear and apparel. These advantages include, but are not limited to: improved flexibility; better regain (elasticity); better impact resistance because the material of the invention absorbs a greater amount of kinetic energy because the material comprises more microspheres per unit area; better dilatency than Nickerson's dispersed microspheres which exhibit little to no dilatency; better dilatency than Schaefer's material because the material of the invention comprises a high number of microspheres per unit volume which translates into a high number of interstices per unit volume which adds to the dilatent strength of the material; decreased backpressure because energy is displaced among a greater number of microspheres; and conformation and deformation properties which are not temperature dependent.

The method of the invention provides a cost-effective, in-line method for shaping and/or molding a polymeric material at room temperature. The method is the result of efforts to design a process which would enable the polymeric material of the invention to be processed into a predetermined shape. Extrusion methods are not feasible because the dilatent properties of the material require such a high degree of pressure, that a device capable of such high pressures would be cost prohibitive. The only previously known method for encapsulating or otherwise shaping highly viscoelastic polymers at room temperature is a manual filling operation whereby a mass of the material is dropped into an envelope or other containment device which can be subsequently sealed.

The preferred protective body apparel, of the invention, comprises: one or more foundation components adapted to be removably worn proximate one or more parts of the body; and one or more pads comprising, a polymeric material capable of absorbing impact energy, which comprises a plurality of microspheres and which is viscoelastic at room temperature, wherein one or more of the pads is carried by one or more of the foundation components. The polymeric material and the microspheres are preferably combined in a ratio of between about 10:1 to about 5:1 by dry weight; and more preferably combined in a ratio of about 7:1 by dry weight. The polymeric material preferably comprises an ester selected from a group consisting of triethylene glycol ester or methyl ester of partially hydrogenated rosin; and may further comprise polyisobutylene, gamma-aminopropyltriethoxysilane, and/or gamma-glycisoxypropyltrimethoxysilane. The microspheres preferably comprise polyacrylonitrile and polymethylmethacrylate, and may further comprise ethylene-vinyl acetate, vinylidene chloride, vinyl chloride and/or acrylonitrile, and combinations thereof having a moisture content of less than 5% by weight.

One or more of the foundation components may comprise one or more pockets adapted to support one or more of the pads; and/or one or more of the pads comprises one or more seam allowances through which the pad is stitched to one or more of the foundation components. One or more of the pads may be carried by one or more alternative or additional means for carrying including, but not limited to, Velcro®, hook and eye, grommet, button, zipper and snap. Further, one or more of the foundation components comprises ballistic-proof armor, including, but not limited to a ballistic-proof vest.

The preferred method of the invention, for processing a dilatent, polymeric material, which is viscoelastic at room temperature and capable of compression regain, into one or more predetermined configurations, comprises the steps of: providing the polymeric material, which is viscoelastic at room temperature and capable of compression regain; introducing an amount of the polymeric material into a flexible sleeve; inserting and running the sleeve, into which the polymeric material is introduced, between one or more pairs of rollers, each roller having at least one outside surface which contacts the sleeve as the sleeve runs between the rollers, to form a sheet of the polymeric material, encased in the sleeve, having one or more surfaces which corresponds to the outside surfaces of one or more of the rollers; wherein the polymeric material preferably comprises a plurality of microspheres and wherein the polymeric material and the microspheres are preferably combined in a ratio of between about 10:1 to about 5:1 by dry weight, and more preferably in a ratio of about 7:1 by dry weight. The polymeric material may comprise an ester selected from a group consisting of triethylene glycol ester or methyl ester of partially hydrogenated rosin; and may further comprise polyisobutylene, gamma-aminopropyltriethoxysilane and/or gamma-glycisoxypropyltrimethoxysilane. The microspheres preferably comprise polyacrylonitrile and polymethylmethacrylate, and may further comprise ethylene-vinyl acetate, vinylidene chloride, vinyl chloride or acrylonitrile or combinations thereof having a moisture content of less than 5% by weight. The outside surface of at least one pair of the rollers is preferably substantially smooth to produce a sheet of the polymeric material wherein the one or more surfaces of the polymeric material, corresponding to the outside surfaces of the rollers, are substantially smooth.

The method may further comprise the steps of die cutting at least a portion of the sheet of the polymeric material into one or more shapes; encapsulating one or more of the shapes in one or more flexible film alone or in combination with other suitable materials, to produce an impact energy absorbing pad, comprising, a polymeric material which is viscoelastic at room temperature, comprises a plurality of microspheres, and has a predetermined configuration. The shapes may be encapsulated by introducing the shapes into one or more whole or partial capsules or between two or more films and sealing any openings, and/or by drawing or pressing the shapes into a film vacuum previously or simultaneously drawn or pressed into a mold.

The sleeve of the sheet may comprise a first thermoplastic material which is preferably flexible, and the method may further comprise the steps of, placing at least a portion of the sheet in contact with at least a portion of a foam material and a second thermoplastic material; and applying a means for causing at least a portion of the first thermoplastic material to adhere to at least a portion of the second thermoplastic material to capture at least a portion of the foam therebetween. The first and second thermoplastic materials preferably comprise polyvinyl chloride, polyurethane, polyolefins such as polyethylene or polypropylene, or other suitable flexible, thermoplastic film materials. The means for causing the first thermoplastic material to adhere to the second thermoplastic material preferably comprises radio frequency or sonic or impulse energy.

The method may also comprise the steps of, vacuum forming and/or drawing at least a portion of the second thermoplastic material into a mold; removing the sleeve from at least a portion of the sheet prior to the vacuum drawing step; die cutting a portion of the sheet, from which the sleeve was removed, to form one or more shapes; introducing one or more of the shapes into the mold with or without one or more layers of foam; and applying a means for adhering the sleeve to the second thermoplastic material, to produce an impact energy absorbing pad, comprising, a polymeric material which is viscoelastic at room temperature and a plurality of microspheres, and has a predetermined configuration.

It is envisioned that materials and methods of the invention may be adapted for any protective gear and apparel which is used to reduce the risk of trauma caused by pressure or sudden impacts. The materials and methods are envisioned for use with bullet-proof vests or jackets and other ballistic-protective gear and apparel; any type of protective clothing apparel used for riot control, corrections activities or apparel or equipment used in connection with martial arts; any type of apparel or article worn on or over any portion of a person or animal; protective gear, including, but not limited to, any type of helmet and shin and elbow guards; gloves; ski boots; snowboarding boots, motorcycle gear; all types of skates including, but not limited to, hockey skates, figure skates, racing skates and inline skates; all types of athletic footwear including, but not limited to, soccer, basketball, rugby, football, tennis, jogging, climbing, cycling; shoes; boots; any other type of footwear; any type of orthopedic cast or brace or the like.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENT AND METHODS OF THE INVENTION

The protective apparel of the invention generally comprises one or more foundation components, such as a vest, which is provided with one or more internal or external overlays or pockets attached in a manner which does not restrict the apparel's flexibility. The overlays comprise one or more pads which comprise a viscoelastic polymeric material encased in a flexible, thermoplastic, heat-sealable film. The pads may further comprise one or more of the following materials: bonded elastic microspheres, a flowable elastomer, foam, gel, liquid, gas or any other suitable padding material. The pads are designed to absorb the energy transmitted by a sudden, external impact.

Figure 1:
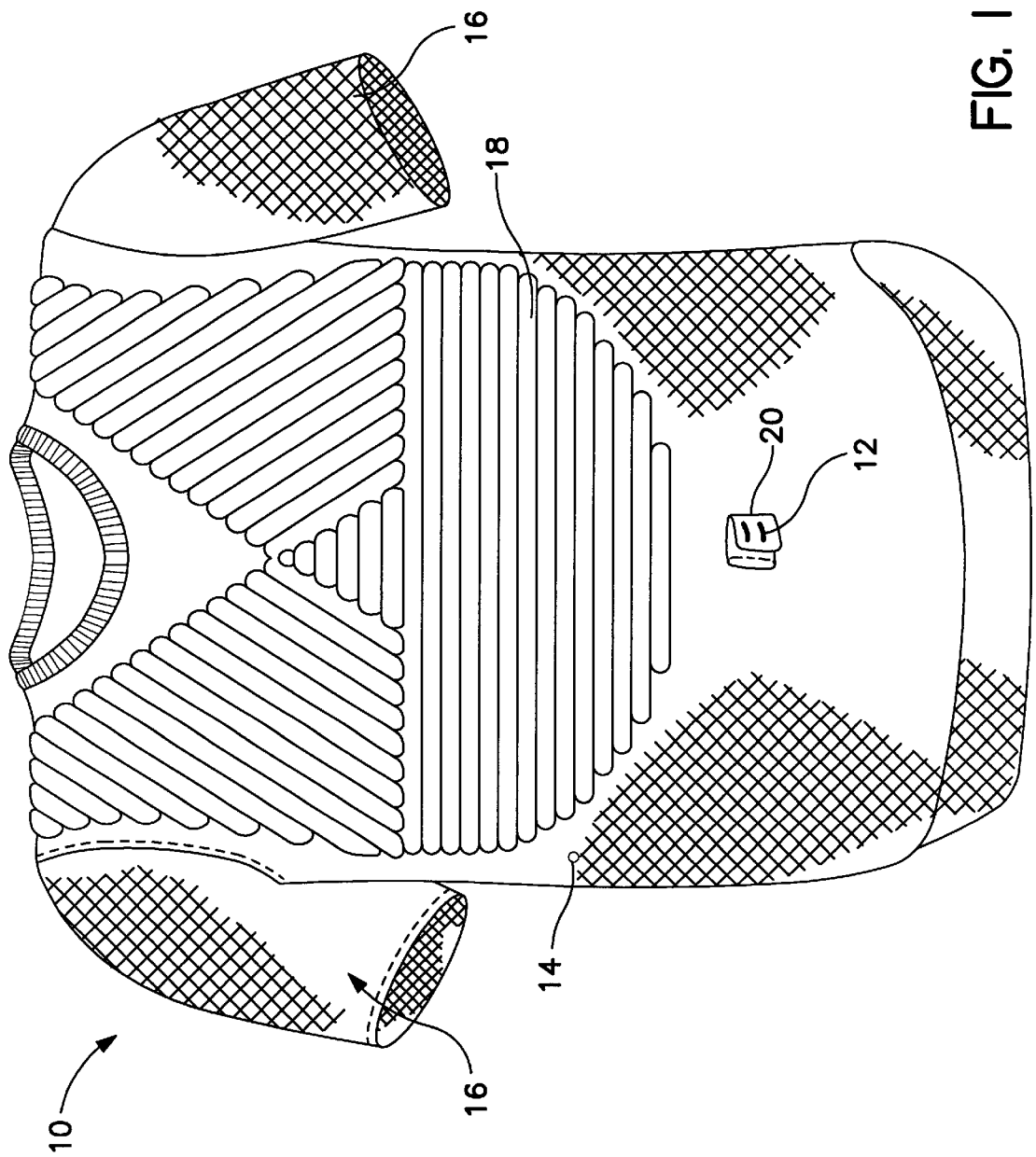
FIG. 1 is a front view of a preferred embodiment of the protective apparel of the invention.

A preferred embodiment of one example of the protective apparel of the invention is shown and generally referred to in FIG. 1 as shirt 10. Shirt 10 is designed to be worn alone or under or over another garment. Shirt 10 generally comprises: vest 14 which generally covers the front and back of a torso, sleeves 16 and a plurality of pads (e.g. pad 18)

positioned to protect the soft tissue and vital organs. Vest 14 acts as the foundation component for the pads. The pads are stitched to vest 14 to hold the pads in position.

Figure 2:
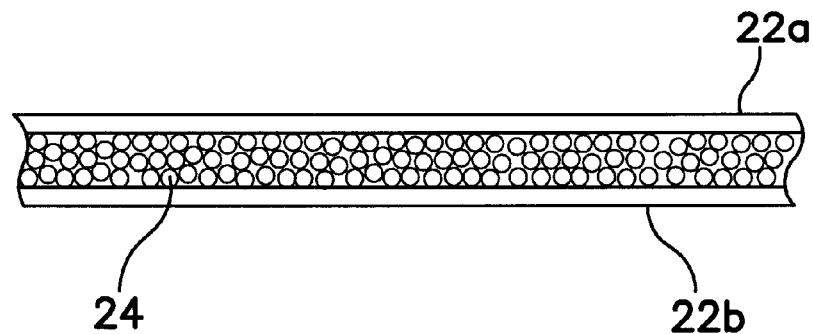
FIG. 2 is a cross-sectional view of a preferred embodiment of the pad of the invention.
Figure 3:
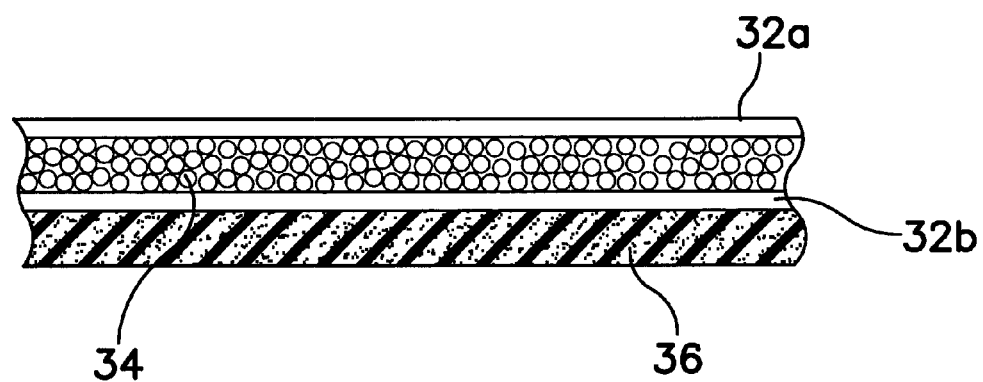
FIG. 3 is a cross-sectional view of the pad of the invention fixed to a layer of foam.

FIG. 2 illustrates one such pad 18. The pad 18 comprises a polymeric material comprises a plurality of microspheres 24 encased in a sleeve defined by sheets 22a and 22b. FIG. 3 illustrates another pad 30. The pad 30 comprises a polymeric material comprises a plurality of microspheres 34 encased in a sleeve defined by sheets 32a and 32b and adhered to a layer of foam 36.

Vest 14 and sleeves 16 may be made of a lightweight mesh, as shown in FIG. 1, to be worn under or over another garment, or may be made of a more substantial material and worn alone as a shirt or jacket. The material used for the foundation component will depend on the application and conditions for which the apparel is intended. Shirt 10 is also provided with tab 20 comprising one or more button holes 12. Tab 20 enables the wearer to button tab 20 to an overlying shirt, jacket or vest to keep shirt 10 from riding up underneath the overlying garment.

The apparel of the invention is not in any way limited to shirt 10 or vest 14. Any number and variety of protective wearing apparel and gear may be adapted to incorporate the protective pads of the invention into their structure. Depending on the application, the foundation component may be provided with one or more partial or whole pockets adapted to carry the pads by supporting or completely enveloping one or more of the pads inside the pocket. The foundation component and/or the pads may alternatively or additionally comprise one or more means for fixing the pads to the foundation component including, but not limited to, Velcro®, hook and eye, grommet, button, zipper and snap.

The foundation component may comprise, or be incorporated into, any type of protective gear or wearing apparel, including, but not limited to ballistic-proof vests or jackets and other ballistic-protective gear and apparel; any type of protective clothing apparel used for riot control, corrections activities or apparel or equipment used in connection with martial arts; any type of apparel or article worn on or over any portion of a person or animal; protective gear, including, but not limited to, any type of helmet and shin and elbow guards; gloves; ski boots; snowboarding boots, motorcycle gear; all types of skates including, but not limited to, hockey skates, figure skates, racing skates and inline skates; all types of athletic footwear including, but not limited to, soccer, basketball, rugby, football, tennis, jogging, climbing, cycling; shoes; boots; any other type of footwear; any type of orthopedic cast or brace or the like.

The pads or cells, in general, should be between about 3/32" and 1" thick, and preferably between about 3/32" and ½" thick. The pads of the invention are preferably made by gluing, bonding or otherwise adhering gas or air filled elastic microspheres with long chain diisobutaines or other suitable materials including, but not limited to, isobutylene and/or esterified resins, stabilized or unstabilized, which exhibit a high degree of dilatency. The ratio of polymeric material to microspheres is preferably between about 10:1 to about 5:1 by dry weight. For device 10, the ratios are about 7:1 and 6:1 by dry weight. The polymeric material preferably comprises an ester selected from a group consisting of triethylene glycol ester or methyl ester of partially hydrogenated rosin; and may further comprise polyisobutylene, gamma-aminopropyltriethoxysilane, and/or gamma-glycisoxypropyltrimethoxysilane. The microspheres preferably comprise polyacrylonitrile and polymethylmethacrylate, and may further comprise ethylene-vinyl acetate, vinylidene chloride, vinyl chloride and/or acrylonitrile, and combinations thereof having a moisture content of less than 5% by weight.

Following are four exemplary formulations of the invention. In the formulations, PAN refers to polyacrylonitrile, PMMA refers to polymethylmethacrylate and EVA refers to ethylene-vinyl acetate. The triethylene glycol ester and methyl ester of partially hydrogenated rosin is available from Hercules Inc. as Staybelite® Ester 3 Synthetic Resin or Hercolyn® D Hydrogenated Ester of rosin; the PAN/PMMA microspheres are available from Nobel Industries as Expancel DE 091; the gamma-aminopropyltriethoxysilane or gamma-glycidoxypropyltrimethoxysilane is available from Union Carbide Chemicals and Plastics Co., Inc., product numbers A-187 and A-1100, respectively; and the EVA microspheres are available from Nobel Industries as Expancel MB 092.

| FIRST EXAMPLE | |
|---|---|
| Triethylene glycol ester or methyl ester of partially hydrogenated rosin | 500 g |
| Microspheres (PANIPMMA) | 75 g |
| TOTAL WEIGHT | 575 g |
| Binder to microsphere ratio (dry) | 6.67:1 |
| SECOND EXAMPLE | |
| Triethylene glycol ester or methyl ester of partially hydrogenated rosin | 400 g |
| Polyisobutylene | 125 g |
| Microspheres (PAN/PMMA) | 75 g |
| TOTAL WEIGHT | 600 g |
| Binder to microsphere ratio (dry) | 7.00:1 |
| THIRD EXAMPLE | |
| Triethylene glycol ester or methyl ester of partially hydrogenated rosin | 400 g |
| Polyisobutylene | 125 g |
| Gamma-Aminopropyltriethoxysilane or Gamma-Glycidoxypropyltrimethoxysilane | 10 g |
| Microspheres (PAN/PMMA) | 85 g |
| TOTAL WEIGHT | 620 g |
| Binder to microsphere ratio (dry) | 6.29:1 |
| FOURTH EXAMPLE | |
| Triethylene glycol ester or methyl ester of partially hydrogenated rosin | 400 g |
| Polyisobutylene | 125 g |
| Gamma-Aminopropyltriethoxysilane or Gamma-Glycidoxypropyltrirnethoxysilane | 10 g |
| Microspheres (PAN/PMMA) | 65 g |
| Microspheres blended with EVA | 25 g |
| TOTAL WEIGHT | 625 g |
| Binder to microsphere ratio (dry) | 5.94:1 |

By coating the microspheres with non-slippery, high friction producing materials, the pads effectively exploit the rate dependent shear characteristics of the material to form a semi-liquid, conforming, energy absorbing masma. The rate of shear created by a high speed impact is substantially increased as each of the individual microspheres attempts to roll over another microsphere. Since the action of rolling over each other multiplies the applied force of shear, the resulting rate of shear at the interface of each microsphere continues to increase. This increases the inherent rate of shear to the point wherein the semi-liquid nature of the material increases its viscosity and rapidly approaches the semi-solid or solid state. The resulting solid, lightweight pad absorbs much more kinetic energy than it could in a semi-liquid state when pressure is applied in a slow, even manner. For example, the viscosity of the masma of the invention increases closer to a non-liquid, nonmovable mass as the rate of shear increases. This effect is pronounced with the high rate of shear associated with high impact blows.

The dilatency of the polymeric material used in the pads does not allow one to change the physical state of the material easily. When a dilatent material is subjected to rapid or high external stress or strain, the material resists flow and instead, increases in volume and/or viscosity and appears to change from a flowable, conformable soft material to a firm, more rigid non-flowable material which offers resistance to the external force to produce an effect of pushing back at a rate higher than that applied by the external force. As such, dilatent materials cannot be easily processed into predetermined shapes using conventional extrusion, filling or pressing methods.

The preferred method of the invention for processing a dilatent polymeric material, which is viscoelastic at room temperature and capable of compression regain, into one or more predetermined configurations, generally comprises the steps of, providing the polymeric material, which is viscoelastic at room temperature and capable of compression regain; introducing an amount of the polymeric material into a flexible sleeve; inserting and running the sleeve, into which the polymeric material is introduced, between two or more pairs of rollers, each roller having at least one outside surface which contacts the sleeve as the sleeve runs between the rollers, to form a sheet of the polymeric material, encased in the sleeve, having one or more surfaces which corresponds to the outside surfaces of the rollers. It is very important that all of the rollers operate at precisely the same speed and that the surface speed of the rollers does not exceed 70 linear feet per minute (lfpm).

Figure 4:
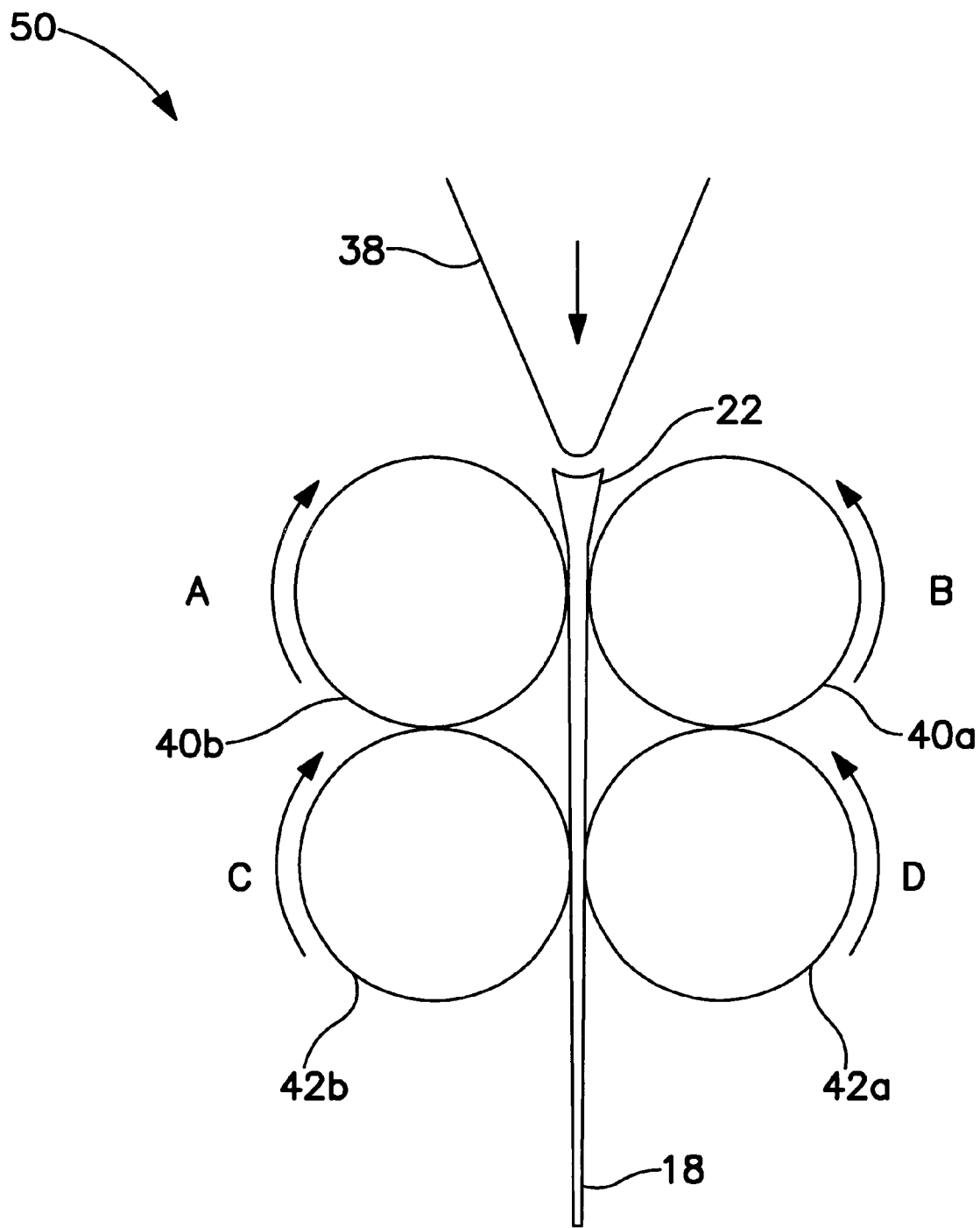
FIG. 4 is a cross-sectional view of the system used to carry out the preferred method of the invention.

The polymeric material of the invention, which is provided in the first step, is made according to the specifications described above. The preferred method of the invention is carried out using system 50 as shown in FIG. 4. The polymeric material is then placed into a hopper 38 and introduced into the flexible sleeve 22. The material may be introduced, either by dropping a predetermined amount into a limited length of sleeving or by continuously introducing the material into an unlimited length of sleeving at a predetermined rate using an auger (not shown). The flexible, plastic sleeve or tube is prepared from any type of flexible plastic sheeting. The sheeting is preferably thermoplastic or thermoset and may comprise one or more components including, but not limited to, polyethylene, polyolefin, polyvinyl chloride and polyurethane. The sleeving can be any desired width and is only limited by the width of the rollers used. The rollers are Teflon® coated comprise a first set of two rollers, 40a and 40b, and may further comprise additional sets of rollers such as the second set of two rollers 42a and 42b shown in FIG. 4. The diameter of the rollers may vary depending on the desired capacity and size of the system. The outside surface of the rollers is preferably substantially smooth to produce a sheet of polymeric material that is substantially smooth and flat.

The rollers are driven in the direction of arrows A–D by an AC or DC motor which is reversible and capable of constant torque at controllable slow speeds of revolution. The gap between each of the two sets of rollers is adjustable and should be adjusted to a gap slightly less than the desired resulting thickness of the pad, preferably between about 70% to 85% of the desired resulting thickness.

The plastic sleeve, having a width the same as the desired resulting width of the pad, is inserted between the first set of rollers at a gap that is between about 20% to 40% greater than the resulting desired thickness. The polymeric material of the invention is introduced into the sleeve and drawn through the rollers at a speed not exceeding 70 lfpm. The filled sleeve than passes through the second set of rollers, at the same rate of speed, with a gap that is between about 70% to 80% of the desired resulting thickness. These steps result in pad 18 comprising a flat, sheet of the polymeric material encased in a plastic sleeve, having a uniform thickness and width that is equal to the predetermined desired width. Depending on the application, the sleeve may then be stripped from the polymeric material resulting in a sheet of the polymeric material having a uniform width and thickness.

The method of the invention overcomes the problems and hurdles previously associated with making and filling plastic envelopes with dilatent, viscoelastic polymeric materials. The sheets of the invention comprise tubes made from a flexible thermoplastic material, such as polyvinyl chloride, polyurethane, metalasine and/or polyolefins, such as polyethylene and polypropylene, into which a polymeric material, having a moisture content that is preferably less than 5%, is introduced. The method of the invention eliminates the need to die cut the material and hand place the cut material onto a sheet or between two or more sheets of flexible, sealable film. The method enables one to make filled envelopes in a single operation. There is no need to separately fill an envelope, no need for a pre-made envelope and no need to seal the envelope after filling.

By reducing the moisture content of the material, the dielectric is also removed, which, together with the thermoplastic film, results in a uniform sheet. This sheet can be die cut into any number of shapes, which, in turn, sealed using radio frequency, ultrasonic or impulse sealing, and/or placed on flat sealable sheets or in preformed cups or shapes. The method of sealing will depend on the type of plastic tubing used. Die cutting and/or sealing may be carried out in-line, downstream from the rollers or at a separate station.

The materials and methods of the invention also allows the polymeric material to be layered or otherwise combined in packages with other materials, such as foam or other viscoelastics. For instance, at least a portion of the sheet of the invention is placed in contact with at least a portion of a foam material and a second thermoplastic film; and applying a means for causing at least a portion of the first thermoplastic material to adhere to at least a portion of the second thermoplastic material to capture at least a portion of the polymeric material and at least a portion of the foam between the first and second thermoplastic materials to form an envelope.

The first and second thermoplastic materials preferably comprise polyethylene, polyvinyl chloride, polyolefin, polyurethane or other such flexible film materials. The means for causing the first thermoplastic material to adhere to the second thermoplastic material preferably comprises radio frequency and sonic or impulse energy. The energy level, time, pressure may be adjusted depending on the type, thickness and unit area of the sheet or die cut piece. A portion of the first thermoplastic material may be removed from the sheet or die cut piece prior to introducing a portion of the sheet into the mold. For example, one entire side of the sheet may be removed so that one side of the polymeric material is placed directly against the second thermoplastic material when the sheet is introduced into the mold. One or more foam materials, other viscoelastic materials or other suitable materials may also be introduced into the mold between or in addition to the polymeric material and the second thermoplastic material.

Auxiliary materials may be used in connection with the pads to augment the pads' function and scope of use, including, but not necessarily limited to, liquids, gases, gels and/or open or closed cell foam, or any other natural or synthetic cushioning or padding material. The shape of the pads and the overall shape and style of the device are not limited to those described above, and may be modified as needed to accommodate the application for which they are intended.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. Protective body apparel, comprising,
   one or more foundation components adapted to be removably worn proximate one or more parts of the body; and
   one or more impact pads comprising, a polymeric material capable of absorbing impact energy, which comprises a plurality of microspheres and which is viscoelastic at room temperature, said polymer material and said microspheres being combined in a ratio of between about 10:1 to about 5:1 by dry weight wherein one or more of said pads is carried by one or more of said foundation components.

2. The apparel of claim 1, wherein said polymeric material and said microspheres are combined in a ratio of about 7:1 by dry weight.

3. The apparel of claim 1, wherein said polymeric material comprises an ester selected from a group consisting of triethylene glycol ester or methyl ester of partially hydrogenated rosin.

4. The apparel of claim 3, wherein said polymeric material further comprises polyisobutylene.

5. The apparel of claim 4, wherein said polymeric material further comprises gamma-aminopropyltriethoxysilane.

6. The apparel of claim 4, wherein said polymeric material further comprises gamma-glycisoxypropyltrimethoxysilane.

7. The apparel of claim 1, wherein one or more of said microspheres comprises polyacrylonitrile and polymethylmethacrylate.

8. The apparel of claim 7, wherein one or more of said microspheres further comprises ethylene-vinyl acetate.

9. The apparel of claim 1, wherein one or more of said foundation components comprises one or more pockets adapted to support one or more of said pads.

10. The apparel of claim 1, wherein one or more of said pads comprises one or more seam allowances through which said pad is stitched to one or more of said foundation components.

11. The apparel of claim 1, wherein one or more of said pads is carried by one or more means for carrying.

12. The apparel of claim 1, wherein one or more of said foundation components comprises ballistic-proof armor.

13. The apparel of claim 12, wherein said ballistic-proof armor comprises a ballistic-proof vest.

\* \* \* \* \*